US00PP11391P

United States Patent [19]

Glenn

[11] Patent Number: Plant 11,391

[45] Date of Patent: May 23, 2000

[54] BLACK TUPELO NAMED 'NXSXF'

[75] Inventor: Michael M. Glenn, Bogart, Ga.

[73] Assignee: Tree Introductions, Inc., Bishop, Ga.

[21] Appl. No.: 09/020,070

[22] Filed: Feb. 6, 1998

[51] Int. Cl.[7] ..... A01H 5/00

[52] U.S. Cl. ..... Plt./216

[58] Field of Search ..... Plt./216

[56] References Cited

U.S. PATENT DOCUMENTS

P.P. 10,676 11/1998 Beat ..... Plt./216

OTHER PUBLICATIONS

Gerhold, et al., eds., Stree Tree Factsheets, Penn State College of Agriculture: p. 80, 1989.

Huxley et al., eds., The New R. H. S. Dictionary of Gardening vol. 3, The Stockton Press: p. 341, 1992.

Plant Systematics, 2nd ed., Samuel B. Jones, Jr. and Arlene E. Luchsinger, pp. 238–239, McGraw–Hill, 1986.

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A black tupelo tree named 'NXSXF' having an upright, conical growth habit with a dense foliage canopy, a dominant leader with uniformly spaced secondary branches extending upwardly, consistent red fall color, leaf spot resistance, and the capability of being reproduced reliably by budding.

6 Drawing Sheets

DESCRIPTION

The present invention relates to a new and distinct variety of *Nyssa sylvatica,* black tupelo, which has been given the varietal name 'NXSXF'.

I discovered the parent tree of my new variety in 1993 as a lined out chance seedling growing in a production field in a cultivated area at Select Trees, Inc. in Bishop, Ga. This initially discovered tree originated as a seedling planted in 1988. In February of 1992, this tree was one and one-fourth inches caliper at six inches above the ground and was transplanted from a liner field to the production field where it was discovered in 1993. In March of 1996, this initially discovered tree was four inches caliper at six inches above the ground and was transplanted to an observation site at Select Trees, Inc. It is now ten years old. As I observed this parent tree of my new variety, the uniqueness of this tree became apparent because of its more upright growing form, tight conical habit, lustrous dark green leaves, consistent red fall color, resistance to leaf spot, and vigorous rate of growth.

I observed this original tree of my new variety for a period of time and believe it is particularly useful in a landscape setting where native, structurally sound, upright tree forms are important, such as along streets, buildings, and in parking areas.

In contrast, commercially cultivated black tupelo is in its entirety represented by seedling material that is extremely variable in growth habit and so difficult to manipulate in production that it is impossible to produce a consistent field of quality trees.

Black tupelo is a large tree that has been noted to mature in excess of fifty feet high and thirty feet wide, or larger, is adaptable to soil and climate, and has a native range from Maine, Ontario, and Michigan to Florida and Texas. There is a need for adaptable and tolerant native trees with consistent red fall color and dark green foliage that can be grown over a wide geographic area. Consequently, a new variety of black tupelo which has a conical habit, lustrous dark green leaves, consistent red fall color, resistance to leaf spot, and fast growth rate is particularly useful.

My new variety has been asexually propagated by budding at my direction. Budding has been accomplished at a nursery in Boring, Oreg., onto seedling *Nyssa sylvatica* understock.

This propagation and observation of the resulting progeny have proven the characteristics of my new variety of to be firmly fixed. Furthermore, these observations have confirmed that my new variety represents a new and improved variety of black tupelo as particularly evidenced by the unique conical growth habit and propensity to maintain a dominant leader and which can reliably be asexually propagated using vegetative propagation techniques.

The accompanying photographs depict the color of the tree and foliage of my new variety as nearly true as is reasonably possible to make the same in a color illustration of this character.

My 'NXSXF' variety of black tupelo tree has not been observed under all growing conditions and thus variations may occur as a result of different growing conditions. The following is a detailed description of my new variety of black tupelo tree with color terminology in accordance with The Royal Horticultural Society Colour Chart (R.H.S.) published by the Royal Horticultural Society of London. The observations are of the parent tree of my variety growing at the Select Trees, Inc. site in Bishop, Ga.

My new variety of black tupelo tree is characterized by its central dominant leader, conical habit, dense foliage, making the tree difficult to see through when foliage is present, and fast growth rate. In observing the tree from 1988 until 1998, I determined the growth rate to be approximately one and one-half times as fast as average seedlings in the same population from which it was selected. In the spring of 1996, the initially discovered tree of my new variety was eight years old and was transplanted from a production field to an observation site at Select Trees, Inc. in Bishop, Ga. In December of 1997, the tree was seventeen feet high and eight feet wide. Its height to width ratio was 2.125. At six inches, the caliper was five and one-fourth inches; and at one foot, the caliper was four and three-fourths inches. This faster growth rate, upright, conical form and densely uniform foliage far and away distinguish my new variety from typical *Nyssa sylvatica* trees. Most black tupelos are somewhat pyramidal in youth often with pendulous branches but become spreading to form an irregularly rounded or flat-topped crown. The national champion black tupelo tree near Barrackville, W. Va., is one hundred thirty-two feet high and seventy-seven feet wide, with a height to width ratio of 1.71.

My new tree maintains a central leader with upright, symmetrical secondary branches forming a conical outline. In contrast, most seedlings do not maintain a central leader. The unique growth habit insures its capacity for use in areas where growing space is restricted, particularly along streets with buildings or sites which will not accommodate a spreading canopy.

Figure 1:
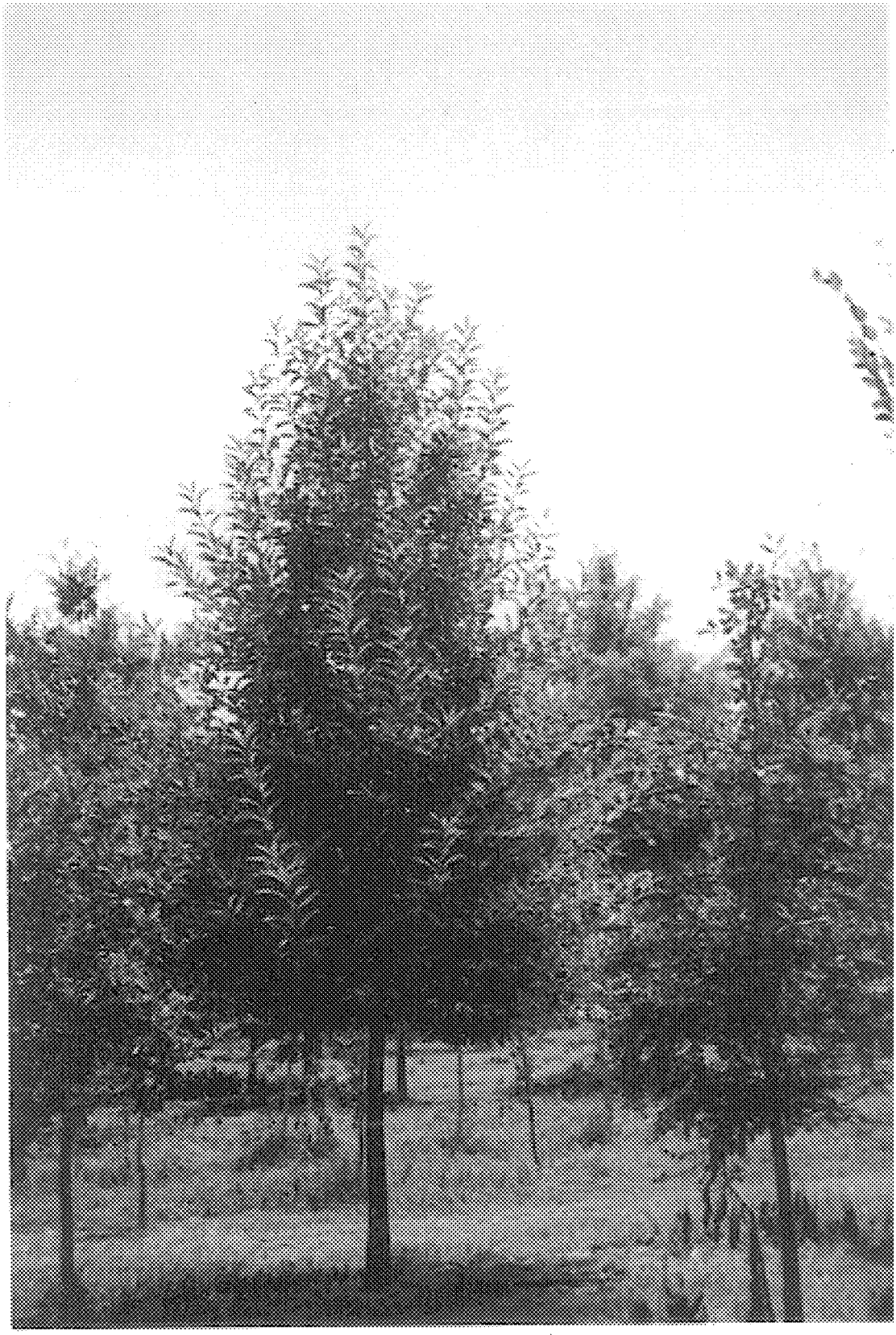
FIG. 1 is a photograph of an entire tree of my new variety.
Figure 2:
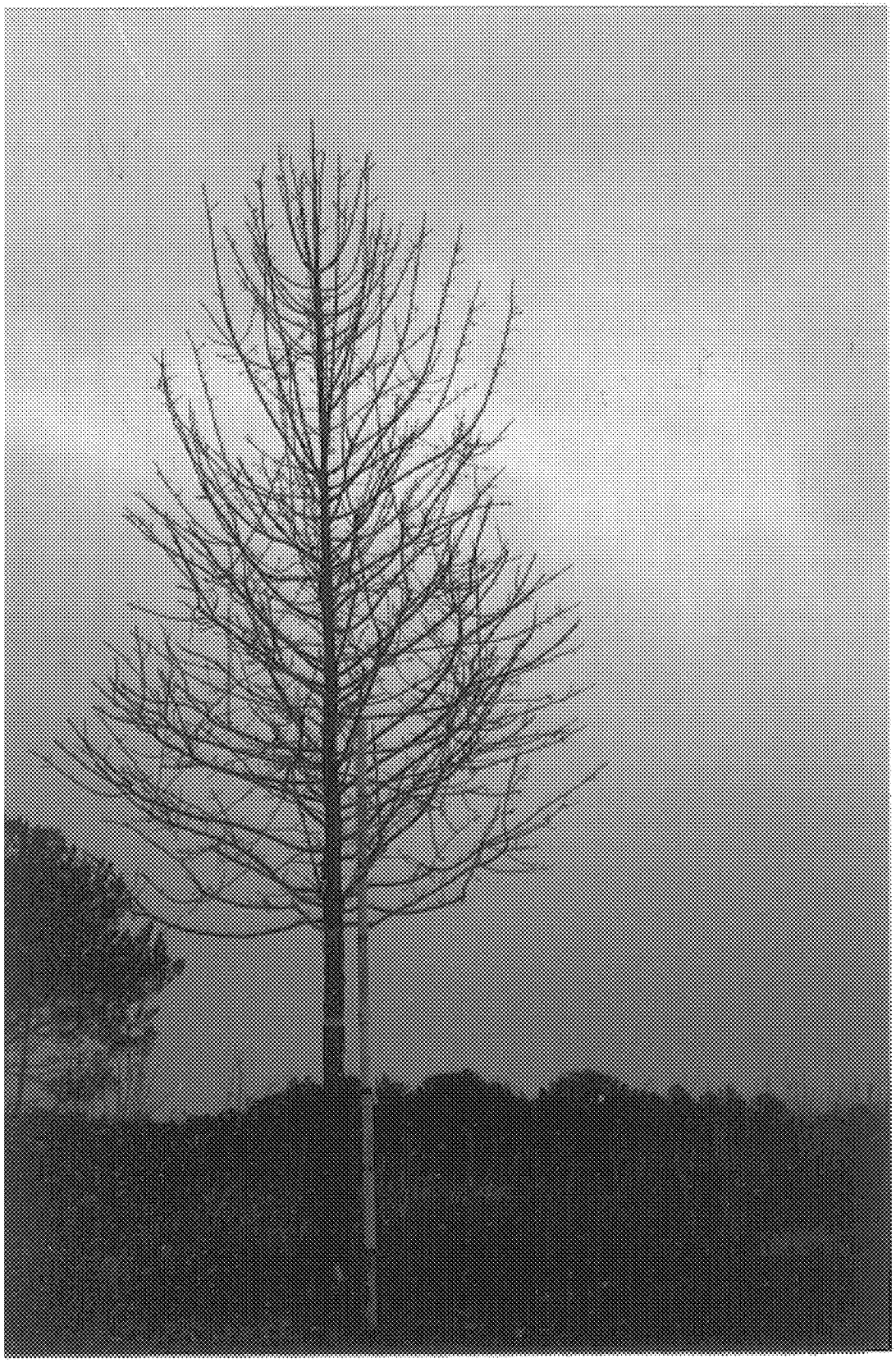
FIG. 2 is a photograph of an entire tree of my new variety showing winter habit and branch structure.

More specifically, my new tree has a branching habit and dendritic pattern of a dominant single leader (bole) with secondary branches that emerge at sixty to eighty degree angles (base) and twenty to thirty degree angles (top) to the central leader. Branches are uniformly borne around the central leader with no large gaps from one branch insertion to the next. As a result, as can be seen from FIG. 1, the tree of my new variety is uniform and symmetrical with a dense canopy. In contrast, traditional seedling black tupelos are open and pendulous and in youth must be trained intensively to produce an upright habit.

Figure 3:
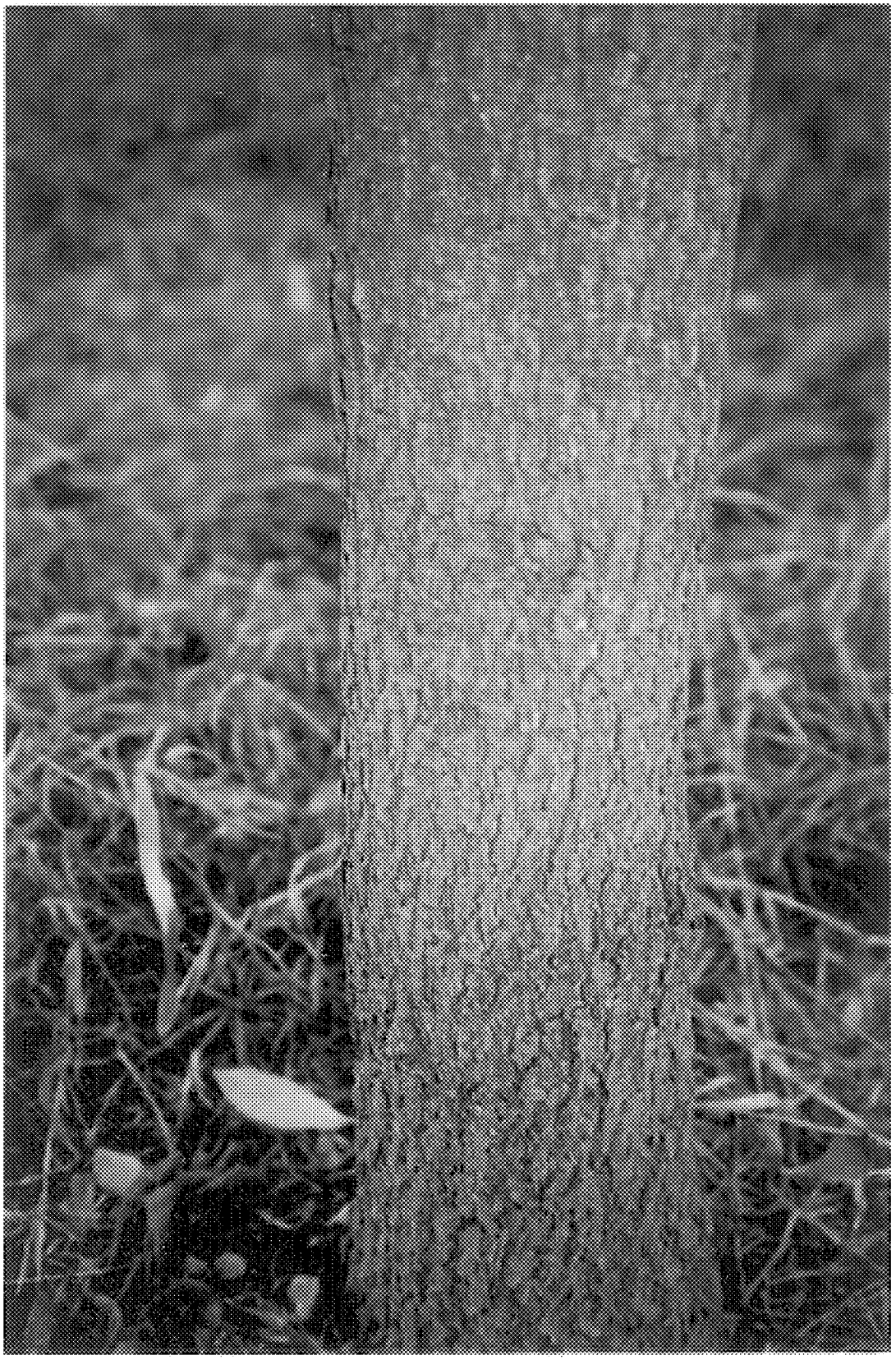
FIG. 3 is a close up of a trunk of my new variety showing mature bark.
Figure 4:
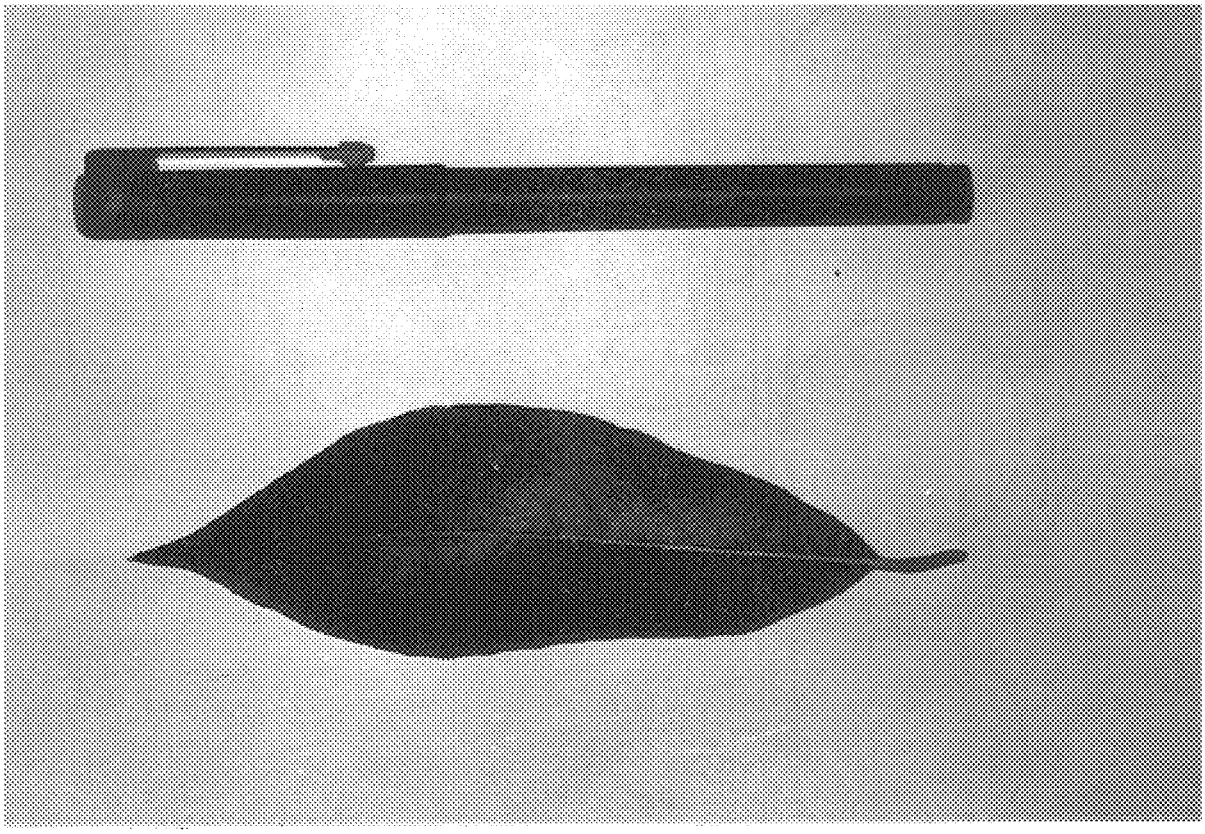
FIG. 4 is a close up of the upper surface of a single leaf from a tree of my new variety.
Figure 5:
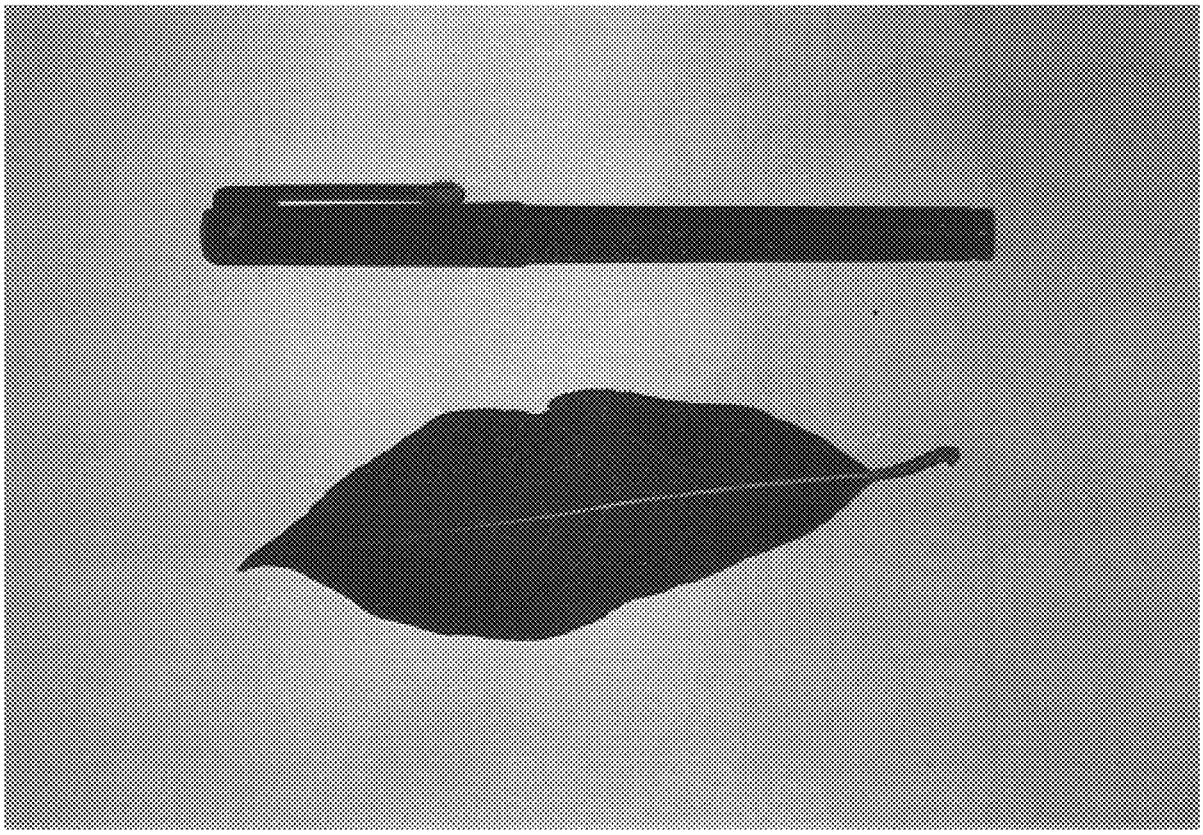
FIG. 5 is a close up of the lower surface of a single leaf from a tree of my new variety.
Figure 6:
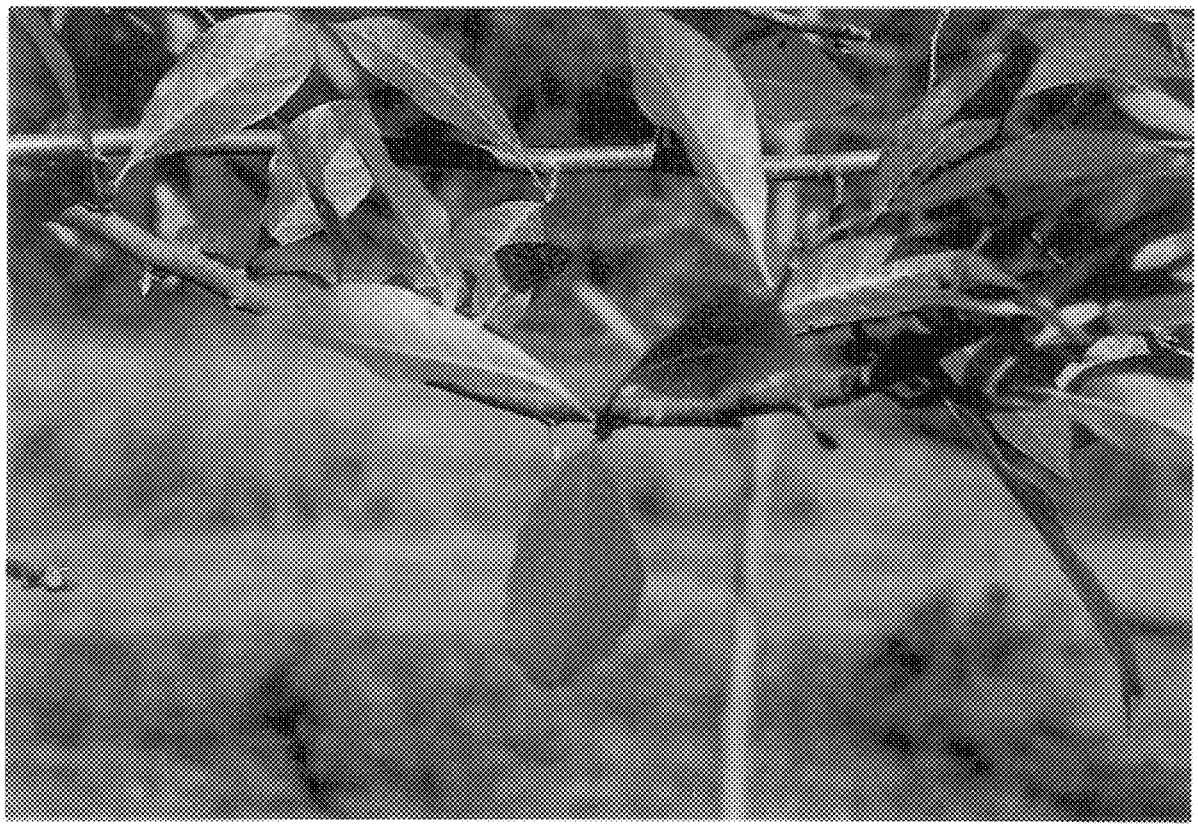
FIG. 6 is a close up of the upper surface of a number of leaves showing the fall color from a tree of my new variety.

The bark of the lower trunk and larger branches is gray-brown (R.H.S. 199C) with ridge and furrowed characters which are grayed-orange (R.H.S. 168A) as shown in FIG. 3. It is assumed that the mature bark will become cross-checked and blocky like that of the species. First year stems are typical of the species.

The upper leaf surface is lustrous dark green (R.H.S. 131A). The lower leaf surface is flat medium green (R.H.S. 136B). In fall, the leaves turn brilliant red (R.H.S. 45B) with veins streaked with yellow (R.H.S. 9B). The mature leaf averages three to six inches long, one and one-half to three inches wide, are elliptic ovate to elliptic obovate with entire margins, and one-half to one inch long petioles. The apices are acuminate and the bases are cuneate.

Flowers and fruits are typical for the species and the new introduction initiated flowers in its seventh growing season.

THE PLANT

Parentage: Chance black tupelo seedling of unknown origin, growing in a cultivated area of Select Trees, Inc. in Bishop, Ga.

Tree shape: Upright conical, densely branched.

Trunk: Sturdy, dominant leader, ridged and furrowed, becoming blocky with age.

Bark: Gray-brown with ridged and furrowed characters which are grayed-orange.

Mature bark color: (Observed in the parent tree) Gray brown (R.H.S. 199C) with grayed-orange (R.H.S. 168A) ridged and furrowed characters.

Branches: Sturdy, ascending, uniformly spaced, emerging from the dominant leader at an angle of sixty to eighty degrees (base) and twenty to thirty degrees (top). Immature branch color like R.H.S. 199A, mature branch color like R.H.S. 197A.

Leaves: Leaf shape is elliptic ovate to elliptic obovate and typical of the species.

Leaf surface: Upper leaf surface is lustrous dark green (R.H.S. 131A) and glabrous. The lower surface is flat medium green (R.H.S. 136B) and glabrous.

Leaf size: Mature leaves average three to six inches long, one and one-half to three inches wide, with one-half to one inch long petioles.

Flowers: Only observed in initially discovered tree, observed to be like those of the species. The flowers are polygamodioecious and appear with the emergence of the leaves. They are small, greenish-yellow, and the females, males and perfect flowers are born in plural flowered, peduncled clusters. The perfect flowers are like the male and female flowers except that they have both a functional pistil and stamens. Most of the flowers on trees of my new variety are female. The fruit is an oblong drupe, ⅜" to ½" long, and bluish-black in color.

I claim:

1. A new and distinct variety of black tupelo tree substantially as herein shown and described, characterized particularly as to novelty by its fast growth rate, unique upright, conical growth habit, uniformly spaced ascending branches, and consistent, red fall color.

* * * * *